United States Patent [19]

Shaw

[11] Patent Number: 5,120,310
[45] Date of Patent: Jun. 9, 1992

[54] NONREUSABLE SYRINGE

[76] Inventor: Thomas J. Shaw, 1510 Hillcrest, Little Elm, Tex. 75068

[21] Appl. No.: 679,627

[22] Filed: Apr. 3, 1991

[51] Int. Cl.$^5$ ............................................. A61M 5/00
[52] U.S. Cl. ................................... 604/110; 604/195
[58] Field of Search ............... 604/110, 187, 195, 198, 604/263, 218, 136, 220

[56] References Cited

U.S. PATENT DOCUMENTS

| | | | |
|---|---|---|---|
| 4,838,869 | 6/1989 | Allard | 604/195 |
| 4,874,382 | 10/1989 | Lindemann et al. | 604/195 |
| 4,904,242 | 2/1990 | Kulli | 604/110 |
| 4,932,940 | 6/1990 | Walker et al. | 604/110 |
| 4,955,870 | 9/1990 | Ridderheim et al. | 604/195 |
| 5,007,903 | 4/1991 | Ellard | 604/195 |

*Primary Examiner*—John D. Yasko
*Attorney, Agent, or Firm*—Hubbard, Thurman, Tucker & Harris

[57] ABSTRACT

A nonreusable syringe is provided having an automatically retracting hypodermic needle to prevent accidental injury after injection or undesirable reuse of the syringe. The needle is retracted by a spring located behind the syringe piston and disposed to prevent reextension of the needle after use. A locking mechanism holds the needle in position for injection. The piston includes means to release the locking mechanism as injection is completed to automatically retract the needle into the syringe. The syringe tip seal is not in frictional contact with the needle, eliminating drag on the needle during retraction.

18 Claims, 2 Drawing Sheets

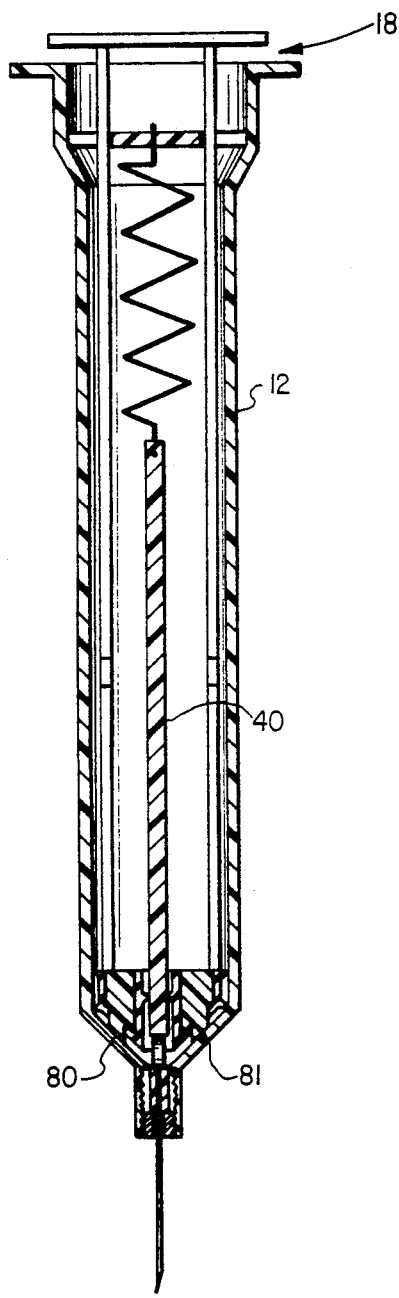
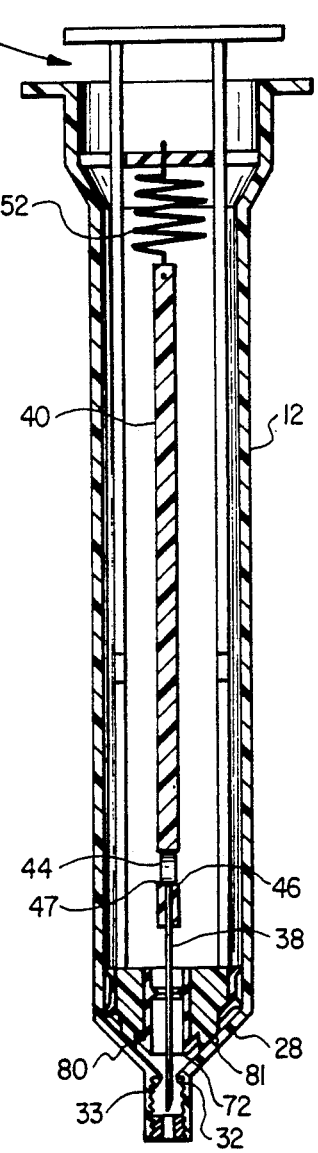
FIG. 4
FIG. 5
FIG. 6

5,120,310

NONREUSABLE SYRINGE

BACKGROUND OF THE INVENTION

This invention relates to a syringe device and more particularly to a nonreusable syringe having an automatically retracting hypodermic needle to prevent reuse of the syringe.

Many communicable diseases are commonly spread by contacting bodily fluids of an infected person. Reuse of hypodermic syringes is one of the most common ways for such contact, particularly among drug users. Various mechanisms are provided in medical facilities for the disposal or destruction of syringes and hypodermic needles after usage. However, it is not uncommon for a medical worker to be scratched or punctured by a needle after usage and before disposal, resulting in injury and exposure to disease.

Various syringes have been devised for retracting the needle into the syringe or otherwise disarming the syringe after it has been used. U.S. Pat. No. 4,874,382 to Lindemann et al. discloses a safety syringe having a needle which is retracted into a protective sheath inside the syringe. After the needle has been used, it may be withdrawn into the sheath by a coil spring which is actuated by the user depressing a trigger mechanism. However, such a device provides no protection against a user desiring to reuse the syringe who would simply not activate the mechanical trigger.

Another device shown in U.S. Pat. No. 4,838,869 to Allard also provides a protective sheath within the syringe into which the hypodermic needle is withdrawn after usage. In this device, depression of the syringe plunger engages protrusions holding the spring loaded needle so as to release the needle for retraction into the sheath. However, the use of a protective sheath substantially reduces the volume available in the syringe for fluid. Moreover, the strength of the spring is substantially limited by restricting its size to the diameter of the sheath, limiting the effectiveness of overcoming friction of the seal against the needle so as to retract the needle. Furthermore, the use of an inner sheath in a syringe restricts the view of the user in detecting undesirable bubbles in the syringe fluid.

SUMMARY OF THE INVENTION

The present invention provides a nonreusable syringe apparatus which overcomes these problems in the prior art. The syringe has a retractable hypodermic needle mounted on a thin rod which extends to a large spring located behind the plunger. Thus, strong retraction force is applied without using syringe fluid space. Also, the hypodermic needle is not in substantial contact with the syringe seal so that there is essentially no friction force to be overcome in retracting the needle. In addition, the needle retracts automatically as soon as the syringe has released all of its fluid, eliminating any chance of accidental injury or intentional reuse of the needle once the fluid has been emitted. Moreover, as retraction begins, the needle breaks the vacuum with the skin so that undesired blood and body fluids are not extracted from the patient as the needle is removed.

In one embodiment, the present invention comprises a spring having a retractable needle for injecting fluid into a body which includes a hollow tubular member providing the cavity for the fluid, a plunger disposed partially within the tubular member having piston means in slidable seal contact with the inner walls of the tubular member to form a chamber for the fluid, needle means in the fluid chamber in sealed contact with one end of the tubular member and having a needle extending therethrough to inject the fluid, resilient means disposed entirely behind the piston means and connected to the needle means, being biased to retract the needle into the fluid chamber, lock means connecting the needle means to the tubular member to maintain the seal contact of the needle means to the tubular member, and release means to automatically disengage the lock means and enable retraction of the needle upon actuation of the plunger.

BRIEF DESCRIPTION OF THE DRAWINGS

FIG. 4 is an elevational cross-section view of the syringe in FIG. 3 with the plunger fully depressed;

FIG. 5 is an exploded detailed view in cross-section of the lower portion of the syringe shown in FIG. 4; and FIG. 6 is an elevational cross-section view of the syringe shown in FIG. 3 in unarmed state with the needle retracted into the syringe cylinder.

DETAILED DESCRIPTION OF PREFERRED EMBODIMENTS

Figures 1, 2, 3:
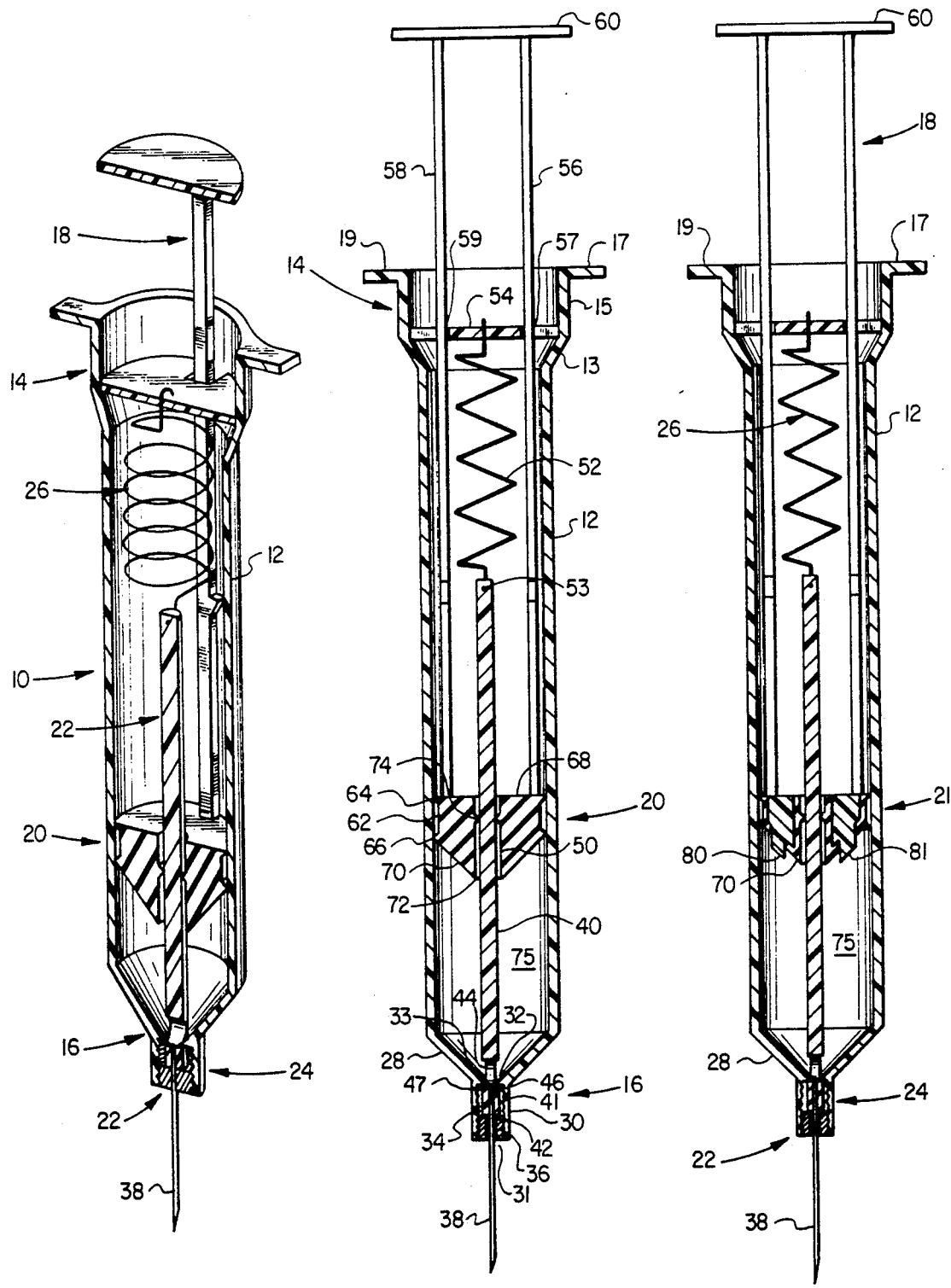
FIG. 1 is a perspective cross-section view of a syringe comprising a preferred embodiment of the present invention.
FIG. 2 is an elevational cross-section view of the syringe of FIG. 1 showing the syringe in armed condition with the needle extended.
FIG. 3 is an elevational cross-section view of another embodiment of the present invention showing the syringe in armed state with the needle extended.

With reference to FIG. 1, a hypodermic syringe 10 is shown comprising a cylindrical tube 12 having an open end 14 and a closed end 16. A plunger assembly 18 extends out of the open end of the syringe tube and is connected to a piston assembly 20 which is slidably movable along the inner walls of tube 12. A needle assembly 22 includes a needle 38 extending through closed end 16 of tube 12. A lock assembly 24 holds the needle assembly in position with needle 38 extended. Needle assembly 22 is connected to a resilient spring assembly 26 which is biased to retract needle assembly 22 into tube 12.

Syringe 10 is constructed to retract needle 22 into tube 12 automatically during the course of use of the syringe as the last step of injecting fluid into a patient. The needle retraction prevents any possibility of infection of a health care worker by accidental contact with the needle after injection. The automatic needle retraction also prevents any further use of the needle for further injections.

Looking now at FIG. 2, tube 12 is preferably a cylinder having a unitary radius throughout except at open end 14 and closed end 16. The radius of tube 12 increases near open end 14 to form an annular ridge 13. Tube 12 extends further at the increased radius to form wall 15 terminating in radially extending fingers 17 and 19.

Closed end 16 of tube 12 is formed by a cone-shaped section 28 in which the radius of tube 12 tapers to form a restricted tube 30 having a small axially centered tubular opening 31. At the point where cone-shaped section 28 joins restricted tube 30, lock tabs 32 and 33 extend radially inward to form a locking mechanism to be discussed later. The interior wall of restricted tube 30 has threads 34 and a threaded tubular tip seal 36 positioned to seal off tubular opening 31.

A hollow sharpened needle 38 extends through restricted tube 30 and tip seal 36. The other end of needle 38 is inset into a rod 40 which extends downward through piston assembly 20 and into tubular opening 31 of tube casing 12. As best seen in FIG. 5, rod 40 has a rod end 41 forming a shoulder 42 which abuts at the end of tip seal 36 thereby sealing off tubular opening 31. Thus needle 38 is not in contact with seal 36, eliminating any frictional pull on needle 38 as it retracts. Needle 38 is inset in rod end 41 and extends to a transverse hole 44 in rod 40 which communicates with the hole in hollow needle 38. At the junction of transverse hole 44 and rod end 41, shoulders 46 and 47 abut against lock tabs 32 and 33, which holds needle 38 in its extended position as shown.

Rod 40 extends axially through a channel 50 in piston 20. A spring 52 is connected through a hole 53 in the end of rod 40 and extends axially to connect to a spring support member 54 resting radially on the slanted annular ridge 13 of tube 12. Preferably, support member 54 is permanently affixed to the walls of tube 12 to prevent removal of needle assembly 22 after use.

Plunger assembly 18 consists of two plunger arms 56 and 58 extending through apertures 57 and 59 in spring support 54 and terminating at piston assembly 20. Plunger bars are connected at their upper end to a flat disk 60 for depressing the plunger during use.

Piston assembly 20 is comprised of a circular piston 62 slidable along the inner walls of tube 12 and having upper and lower annular seals 64 and 66 in slidable contact with the inner walls of tube 12 and forming a fluid seal therewith. Piston 62 has a flat upper surface 68 to which plunger arms 56 and 58 are attached. A conical lower surface 70 slants inward from annular seal 66, ending in an annular tip 72 which forms the lower end of tubular channel 50. Piston 62 also has an annularly extending seal 74 extending within tubular channel 50 to form a fluid seal with rod 40. Thus, a fluid chamber 75 is formed by conical surface 70, annular seal 74, and outer seals 64 and 66 at the upper end. The rest of the fluid chamber 75 is formed by the walls of tube 12 which taper downward in cone-shaped section 28 to restricted tube 30 which is sealed off by tip seal 36 and rod end 41.

An alternate embodiment is shown in FIG. 3 having the same structure as the syringe of FIGS. 1 and 2 except with regard to piston assembly 21. In this embodiment, piston assembly 21 is identical to piston assembly 20, except that it includes dual cusp abutments 80 and 81 protruding downward from conical surface 70 to make contact with cone-shaped section 28 of the syringe tube 12 when the plunger assembly 18 is fully depressed.

Spring support 54 preferably also includes a shipping safety stop (not shown) comprising a rectangular-shaped member resting on top of spring support member 54 so as to impact the lower surface of plunger disk 60. The shipping safety stop is of sufficient height to prevent the plunger assembly 18 from being depressed to the point where piston assembly 20 impacts locking assembly 24 releasing needle assembly 22 to be withdrawn into the tube. The safety stop may also include a spring biased to automatically fold the stop onto spring support 54 once the plunger assembly 18 has been retracted so as to allow a full stroke of the plunger 18 during injection.

Regarding materials, preferably the spring 52 is steel, needle 38 is corrosive-resistant steel, plunger 62 is a medium-soft rubber, tip seal 36 is medium-hard rubber and all other materials are plastic.

The operation of syringe 10 will now be described. As shown in FIG. 3, the plunger assembly 18 is retracted to draw fluid into chamber 75 through hollow needle 38. After fluid is drawn into chamber 75, it may be injected by inserting needle 38 into the body of a patient and by grasping fingers 17 and 19 while pressing on plunger disk 60, thus moving the plunger assembly 18 into the syringe casing 12. During depression of the plunger assembly 18, fluid is forced out of chamber 75 through needle 38 into the patient.

With reference now to FIGS. 4, 5 and 6, when plunger assembly 18 is fully depressed, the dual cusp abutments 80 and 81 impact the cone-shaped section 28 of tube 12. Preferably section 28 is thin-walled and designed to flex ovally when pushed by dual cusp abutments 80 and 81 so as to flex the lock tabs 32 and 33 holding the needle assembly 24 in place. Lock tabs 32 and 33 then release shoulders 46 and 47 of rod end 41, as best seen in FIG. 5. The resulting action enables spring 52 to fully retract rod 40, thereby retracting needle 38 completely within syringe tube 12, as shown in FIG. 6.

In the preferred embodiment shown in FIG. 2, dual cusp abutments 80 and 81 are not included. Upon depression of plunger 18, annular tip 72 impacts lock tabs 32 and 33 directly and flexes them away from shoulders 46 and 47 of rod end 41, thereby enabling retraction of needle 38.

The advantages and improvements of the present invention are now clearly seen. By placing the spring 52 completely behind the piston assembly 20, a larger spring can be used without displacing the volume of fluid chamber 75. Only a small thin rod 40 protrudes into the fluid chamber. Moreover, since the needle 38 is not in contact with seal 36, essentially no friction is present to oppose action of the spring.

An additional advantage with the present invention is that essentially all of the injection fluid is removed from fluid chamber 75 before the needle retraction mechanism is activated. Thus no fluid is lost through the tubular opening 31 after the seal is broken and the needle 38 is retracted. At the same time, the mechanism of the present invention prevents a user from cleaning and reusing the assembly, because the only way to clean the mechanism is to remove all of the fluid in the syringe, which would activate the retraction device. Once the needle has been retracted into the cylinder of the syringe, it cannot be accessed unless the cylinder itself is broken open. Thus, as long as there is no residue within the fluid chamber, one can be assured that the syringe has not been used.

An important advantage of the present invention is that the needle assembly is retracted automatically after all of the fluid has been forced out of the chamber. This automatic action prevents a medical worker or a patient from being inadvertently stuck by the needle after it has been withdrawn from the patient. It also prevents any further undesirable use of the hypodermic syringe by another user. Moreover, as the needle begins to retract at the point when the fluid injection has been completed, the fluid seal is broken and releases a vacuum formed between fluid chamber 75 and the patient, so that no bodily fluid is removed from the patient's body.

Some additional embodiments are included within the scope of this invention. The needle 38 and rod 40 may be combined as a single component. Also lock tabs 32 and 33 may be replaced by an annular lock ring, and dual cusps 80 and 81 may be replaced by an annular abutment. Other obvious variations may be made to the preferred embodiments shown without departing from the spirit of the invention or the scope of the claims.

What is claimed is:

1. A syringe having a retractable needle for injecting fluid into a body comprising:
   (a) a hollow tubular member providing a cavity for the fluid,
   (b) a plunger disposed partially within the tubular member having piston means in slidable sealed contact with the inner walls of the tubular member to form a chamber for the fluid,
   (c) needle means in the fluid chamber in sealed contact with one end of the tubular member and having a needle extending therethrough to inject the fluid,
   (d) resilient means disposed entirely behind the piston means and connected to the needle means, being biased to retract the needle into the fluid chamber,
   (e) lock means connecting the needle means to the tubular member to maintain the sealed contact of the needle means to the tubular member, and
   (f) release means to automatically disengage the lock means and enable retraction of the needle upon actuation of said plunger.

2. The syringe of claim 1 wherein said needle means includes a rod connected to the needle and extending through said piston means to connect to said resilient means.

3. The syringe of claim 1 wherein said lock means comprises first releasable locking means connected to said tubular member at the end of said fluid chamber, and second releasable locking means for engaging said first releasable locking means and being disposed on said needle means.

4. The syringe of claim 1 wherein said resilient means comprises a spring connected between the said needle means and said hollow tubular member.

5. The syringe of claim 1 wherein said release means comprises actuating means on said piston means to engage said lock means upon movement of said piston means to the end of the fluid chamber having said needle extending through said tubular member.

6. The syringe of claim 1 wherein said hollow tubular member comprises a cylinder having an open end through which said plunger extends and a closed end through which said needle extends to form a fluid chamber with said piston means.

7. The syringe of claim 1 wherein said plunger has a first end comprising a handle extending out of said hollow tubular member and a second end comprising a piston in slidable fluid-sealed contact with the inner walls of the tubular member.

8. A syringe for injection of a fluid into a body, said syringe having a retractable hypodermic needle, comprising:
   (a) a hollow tubular member providing a cavity for the fluid including an upper open end and a lower closed end having a small opening for a needle to extend therethrough and having first lock means thereon,
   (b) a plunger member disposed partially within said tubular member including a handle at one end and a piston means at the other end in slidable fluid-sealed contact with the inner walls of said tubular member;
   (c) a hypodermic needle assembly including a needle end extending through the opening in the lower end of the tubular member, second lock means for engaging said first lock means, and a rod end extending through said piston means,
   (d) resilient means connecting the rod end to the tubular member and biased to retract the assembly inward toward the plunger, and
   (e) release means on said piston means for contacting said first lock means to automatically release it from the second lock means and enable retraction of the assembly means upon actuation of said plunger member.

9. The syringe of claim 8 wherein said first lock means comprises a locking protrusion at said small opening of the lower closed end of the hollow tubular member and said second lock means comprises a surface on said needle assembly disposed near the needle end to engage said protrusion.

10. The syringe of claim 8 wherein said hollow tubular member includes a seal disposed in said small opening in contact with said needle assembly to create a fluid seal at said small opening with the first and second lock means engaged.

11. The syringe of claim 10 wherein said needle assembly is in compression contact with said seal so that substantially no friction is created in breaking contact with said seal.

12. The syringe of claim 8 wherein said resilient means comprises a spring support engaging said hollow tubular member near its upper open end and a spring connected between said spring support and said rod, said spring being biased to retract the hypodermic needle assembly inward toward the plunger.

13. The syringe of claim 8 wherein said release means comprises a protrusion extending from said piston means for contacting said first locking means as said piston means is disposed near the small opening for said needle in said fluid chamber to thereby engage and release said first and second lock means from each other.

14. The syringe of claim 13 wherein the protrusion is an annular tip extending to impact said first locking means and force it apart from said second locking means.

15. The syringe of claim 13 wherein the protrusion comprises dual cusps extending to contact the walls of the tubular member near the lower end to flex said walls and thereby force apart the first and second locking means.

16. A medical device having a retractable needle for injecting fluid into a body comprising:
    (a) a hollow tubular cylinder having an upper open end and a lower end with tapered walls and a tubular axially-centered opening at the end having a seal therein,
    (b) a piston disposed within said tubular cylinder in slidable fluid-sealed contact with the inner walls of the cylinder,
    (c) a plunger attached to said piston and extending out the upper open end of the tubular cylinder for sliding the piston within the cylinder,
    (d) a needle assembly within said tubular cylinder having a needle extending through the opening in the lower end of the tubular cylinder adjacent the seal and a member extending through the piston in sealed contact therewith, (e) a spring connected between the member of the needle assembly and the cylinder tube and biased to exert a retraction force on the needle assembly with the needle extending out said opening in the lower end, (f) locking means for holding said needle assembly with the needle extended through said opening while the piston is distant from the lower end of the tubular cylinder, and (g) release means on the piston for releasing said locking means when the piston is fully extended to contact the lower end of the tubular member.

17. The medical device of claim 16 wherein the release means comprises a protrusion extending from the piston to make contact with the locking means and thereby release the needle assembly to be retracted by the spring.

18. The medical device of claim 16 wherein the release means comprises a protrusion extending from the piston to contact the walls of the lower end of the tubular member causing the walls to flex and thereby releasing the locking means.

* * * * *